(12) United States Patent
Zimmermann

(10) Patent No.: US 7,579,831 B2
(45) Date of Patent: Aug. 25, 2009

(54) TEST DEVICE FOR TUBULAR SPECIMENS

(75) Inventor: Bernd Zimmermann, Ihringen (DE)

(73) Assignee: Prueftechnik Dieter Busch AG, Ismaning (DE)

( * ) Notice: Subject to any disclaimer, the term of this patent is extended or adjusted under 35 U.S.C. 154(b) by 88 days.

(21) Appl. No.: 11/862,356

(22) Filed: Sep. 27, 2007

(65) Prior Publication Data
US 2008/0079427 A1  Apr. 3, 2008

(30) Foreign Application Priority Data
Sep. 28, 2006 (DE) .................. 10 2006 046 339

(51) Int. Cl.
*G01N 27/82* (2006.01)
(52) U.S. Cl. ...................... 324/240; 324/228
(58) Field of Classification Search ............ 324/228, 324/232, 235, 237–243
See application file for complete search history.

(56) References Cited

U.S. PATENT DOCUMENTS

| 3,504,276 | A |   | 3/1970 | Proctor et al. |         |
|-----------|---|---|--------|----------------|---------|
| 5,914,595 | A | * | 6/1999 | Piriou et al.  | 324/220 |
| 6,891,380 | B2| * | 5/2005 | Kesil et al.   | 324/635 |

| 2001/0054896 | A1 | * | 12/2001 | Mednikov et al. | 324/225 |
| 2003/0193329 | A1 | * | 10/2003 | Relton et al.   | 324/235 |
| 2006/0001420 | A1 | * | 1/2006  | Beck et al.     | 324/240 |
| 2007/0222439 | A1 | * | 9/2007  | Wang et al.     | 324/242 |

FOREIGN PATENT DOCUMENTS

| DE | 10 2004 035 174 A1 | 2/2006 |
| GB | 2 014 317 A        | 8/1979 |
| GB | 2 034 049 A        | 5/1980 |
| WO | 2006/067369 A1     | 6/2006 |

OTHER PUBLICATIONS

International Search Report Issuede by the European Patent Office Dated Feb. 7, 2008.

* cited by examiner

*Primary Examiner*—Bot L LeDynh
(74) *Attorney, Agent, or Firm*—David S. Safran; Roberts Mlotkowski Safran & Cole, P.C.

(57) ABSTRACT

A test device for testing of tubular specimens has a plurality of individual, radially movable, finger-shaped test probes which are placed from all sides on the outside of the specimen to be tested. In this way, the test specimen is surrounded by test probes and can be pushed under them. Each test probe has a first test coil with a surface which faces essentially parallel to the lengthwise axis of the specimen and a second test coil which is oriented essentially perpendicular to the lengthwise axis of the specimen. The test probes can be elastically deflectable, pivotably movable, or movable by a screw mechanism.

12 Claims, 3 Drawing Sheets

TEST DEVICE FOR TUBULAR SPECIMENS

BACKGROUND OF THE INVENTION

1. Field of the Invention

This invention relates to a test device for nondestructive testing of tubular specimens. The test device uses a device and a process for detecting defects in these specimens by means of magnetic stray flux sensors.

2. Description of Related Art

Devices of the initially mentioned type are conventionally known. They consist of a host of test coils which are located annularly around the specimens and which are installed in a holding device. In this arrangement, the user has the choice of making either the diameter of the through opening through the arrangement of the test coils larger than the diameter of the specimens, or with a matched diameter of the arrangement of the test coils, accepting major wear on the arrangement of test coils. As the diameter of the arrangement of test coils becomes larger, the distance of the individual test coils from the surface of the specimen increases. Thus, the sensitivity of the measurement arrangement is reduced. Therefore, the layout of an arrangement of test coils of conventional design is always a compromise between measurement precision on the one hand and acceptable costs for replacement of the arrangement of test coils on the other. Replacement of the test coil arrangement becomes necessary when, for example, the specimens does not pass exactly centrally through the opening in the arrangement of test coils or raised faults on the surface of the specimens damage the arrangement of test coils.

SUMMARY OF THE INVENTION

This invention is designed to provide improved sensors for detecting faults in tubular specimens.

This object is achieved by a test device for testing of tubular specimens being devised in which there is a host of individual test probes which can move radially relative to the outside of the tubular probes, each test probe, on the one hand, having a test coil with a surface which faces perpendicular to the lengthwise axis of the specimen, and on the other hand furthermore each test probe having a second test coil with a surface normal which is oriented, essentially parallel to the lengthwise axis of the specimen. In one embodiment of the invention, the test probes are attached to finger-shaped, elastic holding devices of hard metal provided with mechanical pretensioning and by means of these devices the test probes are protected against impact and abrasion by the specimen. In another embodiment, the rigid, finger-shaped holding devices of the test probes are pivotally supported or are supported in another way the permits radial movement. Another embodiment calls for controlling the rotary or radial motion so that the test probe in its finger-shaped holding device always adjoins the tubular specimen.

In particular, the invention is advantageously used to test larger steel and iron pipes, for example, those which are used for petroleum transport (pipelines). The invention is suited especially to detection of defects on the indicated pipes which extend rather transversely to the lengthwise axis of the pipe.

The invention is explained in detail below with reference to the accompanying drawings.

DETAILED DESCRIPTION OF THE INVENTION

Figure 1:
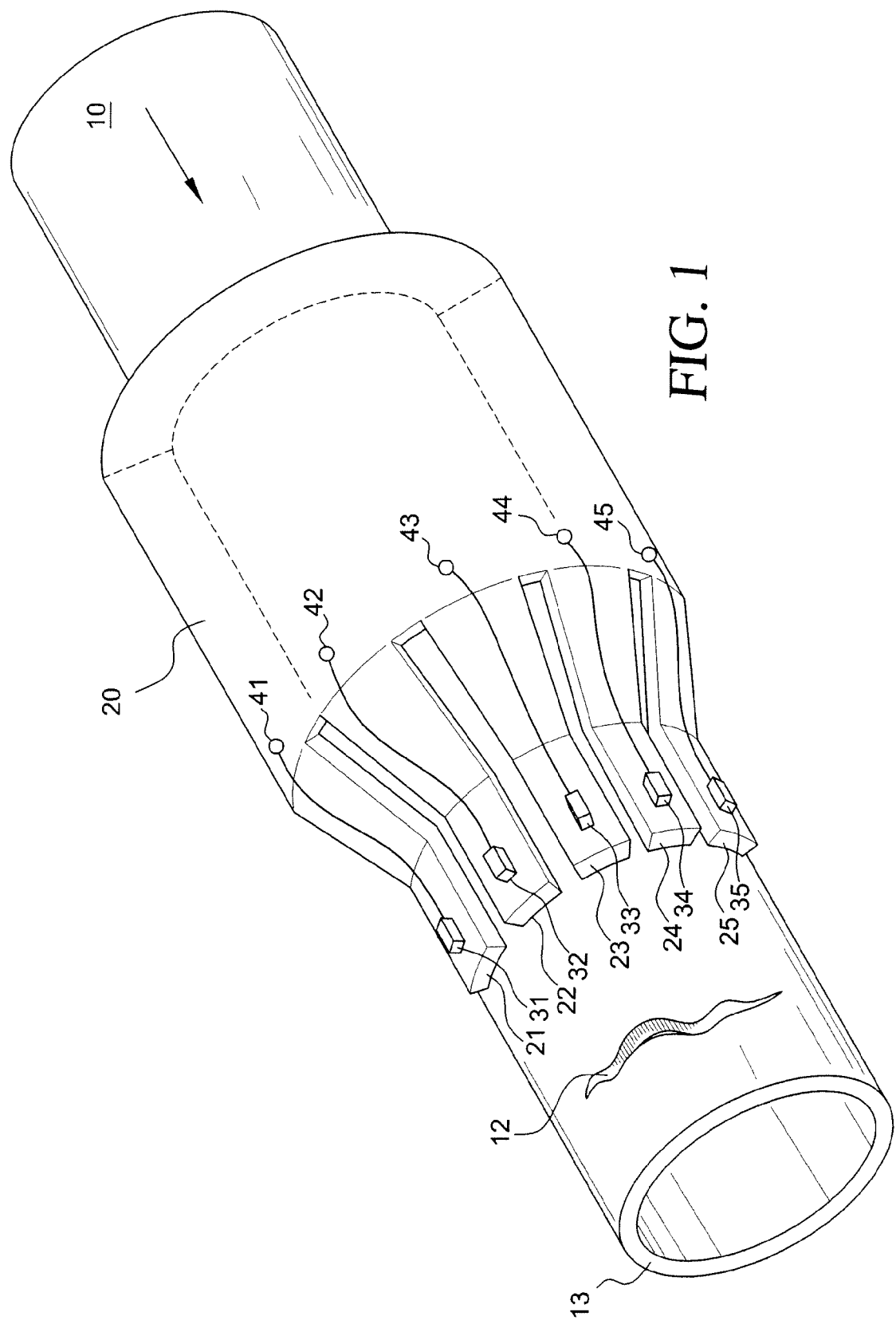
FIG. 1 is a perspective of an example of a tubular specimen with a pipe wall having a transverse defect.

FIG. 1 shows a sensor carrier 20 which is slotted and shaped by bending such that a number (for example, 4 to 8), finger-shaped sensor holding devices 21-25 are provided. The finger-shaped sensor holding devices 21-25 are formed such that the sensor holding devices have elastic pretensioning and allow the attached sensors 53 for detection of magnetic stray flux quantities to rest elastically on the specimens. Furthermore, the forming is such that the sensor holding devices 21-25 are located on an imaginary cylindrical surface around the specimen, as shown in the figure.

In accordance with the invention, a number (normally 2, 3, 4, or 8) of individual sensor carriers 20 is mounted on a holding device so that the sensor carriers surround the entire pipe periphery. According to one embodiment of the invention, the sensor carrier 20 is suited to being shaped by bending around its lengthwise axis such that it can be inserted into holding devices which are made of different sizes. Thus, with only a few sizes of the sensor carriers or sensor holders, test devices for many different pipe diameters (preferably in the range of 60 mm to 370 mm) can be provided. In this way, for each pipe diameter, a respective holding device is necessary, but the individual sensor carriers 20, sensor holding devices 21-25 with the pertinent sensors can be used for several different pipe diameters.

In another advantageous configuration of the invention, the sensor carriers 20 and sensor holding devices 21-25 are not made from one part. Thus, it becomes possible to exchange individual sensor holding devices 21 between different sensor carriers 20, the sensor carriers 20 being matched to a certain pipe diameter or a number of different pipe diameters. If the sensor carriers 20 are made deformable, the number of required sensor carriers is reduced in the transition to a corresponding smaller pipe diameter. For rigid sensor carriers 20, for each pipe diameter, its own type of sensor carrier is necessary. There are contact devices 31-35 so that electrical outputs of the sensors used can be connected to connecting cables which, for their part, are connected to contact devices 41-45 which are indicated symbolically.

Thus, the arrangement shown in FIG. 1 is suited to scanning a tubular specimens, especially in its lengthwise direction, as is indicated by the arrow in FIG. 1.

It is advantageous to arrange two of these devices which are shown in FIG. 1 in succession in the transport direction. Then, continuous scanning of the entire pipe periphery is possible by the individual sensors, the sensors on the second device being circumferentially offset relative to the sensors of the first device such that they detect the areas in the gaps between the sensors of the first device.

Furthermore, when using the same size of sensor carriers and sensors for different pipe diameters, it can happen that the distance of two sensors is too large because the maximum possible number of sensors per pipe diameter is determined by the ratio of the width of the sensor carrier to the pipe periphery. Therefore, at the same size of the sensor holding device 21-25 and sensor carrier 20, for different pipe diameters, there are different distances between the individual sensors. In particular distances can also occur which are actually too large for continuous scanning of the surface of the specimens. In these cases, continuous determination of defects becomes possible when two of these devices are arranged in succession. Furthermore, more accurate determination of the size of a defect in the specimens is possible if so desired.

Figure 2:
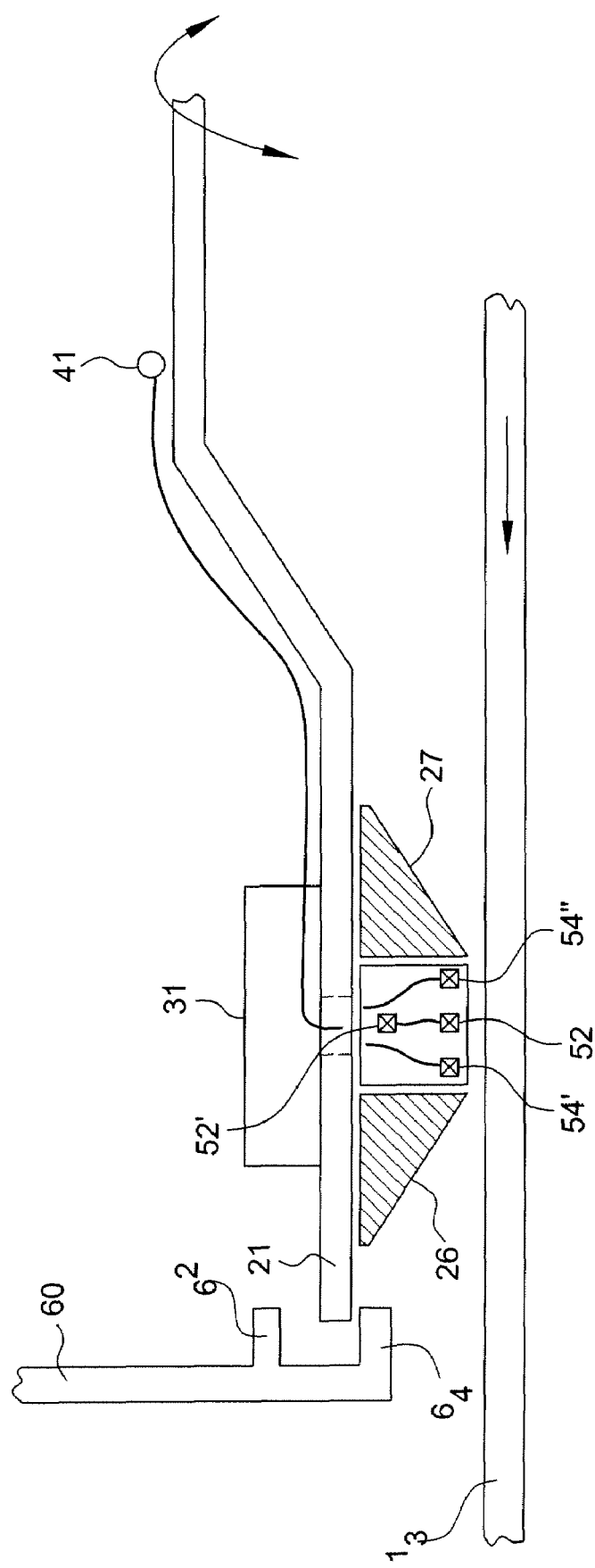
FIG. 2 is a representation of a sensor holding device and an actual sensor.

The actual sensor 53 shown in FIG. 2 contains sensor coils 52, 52' and 54', 54" which are located each on the bottom of the sensor holding devices for detection of magnetic stray flux quantities, as is shown in FIG. 2. In principle, there are sensor coil combinations formed of a respective coil which lies flat with turns 54', 54" (which are shown in cross section) and with an axis which runs radially relative to the specimen, and a respective coil which is perpendicular thereto, i.e., upright, with turns 52, 52' with an axis which runs parallel to the transport direction of the specimen 10. Both the coil 52, 52' which lies flat and also the coil 54', 54" which stands upright extend, superficially, over almost the entire width of the sensor holding device (for example, 21).

To protect against damage of the coils, there are hard metal pieces 26, 27. Furthermore, there are stops 62, 64 on a holder 60 in order to limit the range of motion of the sensor holding device in the radial direction.

As a result of the mechanical pretensioning of the sensor holding devices (for example, 21-25) or another mechanism, as is described below or in conjunction with FIG. 3, the coils 52, 54 which are embedded in a suitable material normally rest directly on the probes or the surface of the pipe 10. It is also possible to make the sensor coil 54 as a flat coil, i.e., a flat spiral, with an axis facing radially away from the specimen and accommodating the magnetic field component which runs radially toward the specimen. The winding of this coil can also, for example, assume the shape of a flat spiral of conductive material applied to a circuit board.

Instead of the elastic configuration of the sensor holding devices, pivotally mounted, rigid sensor holding devices can also be pressed by means of elastic members, compressed air, motorized control or another type of control, in order to ensure the maximum sensitivity of the individual sensors. The pivotable support or elastic action is indicated by the double arrow 69 in FIG. 2. A control which undertakes movement of pivotally mounted sensor holding devices by a motor is likewise possible, detection of the relative position of the sensors relative to the specimens taking place by means of photoelectric detectors, inductive sensors, or other suitable sensors.

Figure 3:
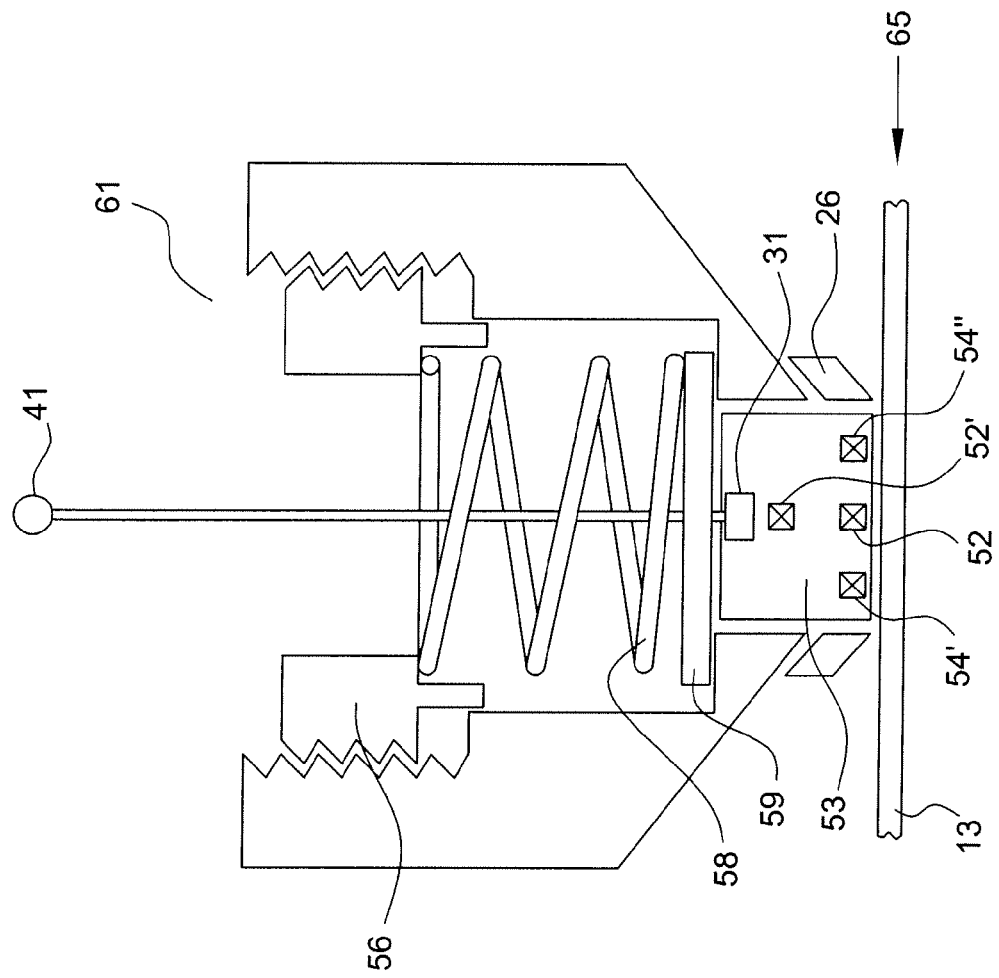
FIG. 3 shows an especially space-saving arrangement of a sensor holding device.

FIG. 3 shows an especially space-saving model using an individual sensor holding device as an example. In this connection, the individual sensor holding devices 61 are made in the form of pipes which run radially relative to the tubular specimen 10, and thus, require less space in the transport direction of the tubular specimen than for the embodiment shown in FIG. 1. Here, the sensors 52, 52' and 54', 54" are protected by a ring-shaped hard metal piece 26. As in FIGS. 1 & 2, there is a contact device 31 via which sensor signals are supplied and extracted for the individual sensors by a connecting cable. Within the pipe, therefore, on the side of the sensor radially away from the specimen, besides the contact device 31, there is an alignment device 59 which, in interplay with devices on the sensor holding device 61 (not shown) provides for correct axial alignment of the sensors. The sensor itself is pressed against the wall 13 of the specimen 10, for example, by means of a helical spring 58. Adjustment of the pressing force is enabled, for example, by a screw 56.

The connecting cable runs in a hole of this screw 56 (shown running between the contact device 31 and the contact device 41 in FIG. 3). When there is control of the distance of the sensors from the wall 13 of the specimen 10, it can be moved with compressed air or also via a linear motor or spindle drive in the tubular sensor holding device 61. In this embodiment, the space requirement for two of these devices in succession for continuous coverage of the specimens is especially small.

Besides the two embodiments shown in FIGS. 1 & 3, in which the fingers run parallel or perpendicular to the transport device, it can be a good idea for the fingers to have a different orientation relative to the transport direction.

The modular structure of the test device formed of the sensor holding device 21-25, the sensor carrier 20 and the holding device 60 enables a significant reduction of the diversity of parts. Sensor wear is reduced by the elastic holding device or the control of the distance from the sensor to the specimen. Furthermore, in this way, simple replacement of individual sensors in the case of a defect which can occur after wear of the hard metal becomes possible. For the test heads for stray flux measurements on pipes which have been available to date, for each defect of an individual coil, the entire test head must be replaced since all sensors are potted in the test head. Therefore, the prior devices always required replacement of all coils regardless of whether some of them are still functional.

What is claimed is:

1. Test device for testing of tubular specimens, comprising a plurality of individual, radially movable test probes, each test probe having a test coil with an axis which is directed perpendicular to a lengthwise axis of the specimen and a second test coil with an axis which is directed essentially parallel to the lengthwise axis of the specimen;

wherein the test probes are mounted on radially movable probe carriers which are located at a plurality of locations circumferentially spaced around an imaginary cylindrical surface and which elastically pretension the test probes in a radially inward direction toward a specimen located within said imaginary cylindrical surface.

2. Test device in accordance with claim 1, wherein the probe carriers on which the test probes are located are finger-shaped, probe carriers which extend essentially parallel to the lengthwise axis of the specimen.

3. Test device in accordance with claim 2, wherein the coil with an axis which is directed perpendicular to the tubular specimen is a flat spiral.

4. Test device in accordance with claim 3, wherein the coil with an axis which is directed radially relative to the tubular specimen has a spiral winding.

5. Test device in accordance with claim 1, wherein the test probes are located on finger-shaped probe carriers which extend essentially perpendicular to the lengthwise axis of the specimen.

6. Test device in accordance with claim 5, wherein the coil with an axis which is directed perpendicular to the tubular specimen is a flat spiral.

7. Test device in accordance with claim 6, wherein the coil with an axis which is directed radially relative to the tubular specimen has a spiral winding.

8. Test device in accordance with claim 2, wherein the finger-shaped, probe carriers are elastically deflectable.

9. Test device in accordance with claim 2, wherein the finger-shaped, probe carriers are pivotally mounted to a holder.

10. Test device in accordance with claim 5, wherein the test probes are radially movable by a screw device.

11. Test device for testing of tubular specimens, comprising a plurality of individual, radially movable test probes, each test probe having a test coil with an axis which is directed perpendicular to a lengthwise axis of the specimen and a second test coil with an axis which is directed essentially parallel to the lengthwise axis of the specimen; wherein hard metal pieces are provided next to the test probes to protect against damaging of the coils.

12. Test device for testing of tubular specimens, comprising a plurality of individual, radially movable test probes, each test probe having a test coil with an axis which is directed perpendicular to a lengthwise axis of the specimen and a second test coil with an axis which is directed essentially parallel to the lengthwise axis of the specimen; wherein the test probes are mounted on radially movable probe carriers, further comprising a holder with stops which limit the range of radial movement of the probe carriers.

* * * * *